United States Patent
Goh et al.

(10) Patent No.: US 11,857,386 B2
(45) Date of Patent: Jan. 2, 2024

(54) MANUFACTURE OF A DENTAL TOOL

(71) Applicant: Prima Dental Manufacturing Limited, Gloucestershire (GB)

(72) Inventors: Wan Tsin Goh, Bristol (GB); Lukasz Dabrowski, Gloucestershire (GB)

(73) Assignee: Prima Dental Manufacturing Limited, Gloucestershire (GB)

( * ) Notice: Subject to any disclaimer, the term of this patent is extended or adjusted under 35 U.S.C. 154(b) by 80 days.

(21) Appl. No.: 17/509,328

(22) Filed: Oct. 25, 2021

(65) Prior Publication Data

US 2023/0126590 A1    Apr. 27, 2023

(51) Int. Cl.
| | | |
|---|---|---|
| *A61C 3/02* | (2006.01) | |
| *A61B 17/00* | (2006.01) | |
| *A61C 13/00* | (2006.01) | |
| *B23C 3/32* | (2006.01) | |
| *B23C 5/10* | (2006.01) | |

(52) U.S. Cl.
CPC ............ *A61C 13/0022* (2013.01); *A61C 3/02* (2013.01); *B23C 3/32* (2013.01); *B23C 5/1009* (2013.01); *A61B 2017/00526* (2013.01); *B23C 2210/40* (2013.01)

(58) Field of Classification Search
CPC ......... A61C 13/0022; A61C 3/02; B23C 3/32; B23C 5/1009; B23C 2210/40
See application file for complete search history.

(56) References Cited

U.S. PATENT DOCUMENTS

| | | | |
|---|---|---|---|
| 7,322,105 B2 * | 1/2008 | Lewis | ...................... B23C 3/36 |
| | | | 433/102 |
| 7,876,454 B2 * | 1/2011 | Du | ........................ G01B 11/24 |
| | | | 356/601 |
| 11,486,456 B2 * | 11/2022 | Jo | ............................ F16D 65/22 |
| 2003/0231934 A1 | 12/2003 | Kienzle | |
| 2007/0116532 A1 * | 5/2007 | Lewis | ................... B21C 37/045 |
| | | | 409/131 |
| 2012/0079918 A1 | 4/2012 | Gensert | |
| 2019/0388979 A1 | 12/2019 | Sinnott | |
| 2020/0263749 A1 * | 8/2020 | Jo | ......................... F16D 65/561 |

FOREIGN PATENT DOCUMENTS

| | | |
|---|---|---|
| GB | 2573524 A | 11/2019 |
| JP | H03104549 A | 5/1991 |
| WO | 9803127 A1 | 1/1998 |
| WO | 0043154 A1 | 7/2000 |
| WO | 2019197931 A1 | 10/2019 |

* cited by examiner

*Primary Examiner* — Lawrence Averick
(74) *Attorney, Agent, or Firm* — Levenfeld Pearlstein, LLC

(57) ABSTRACT

A method for manufacturing a dental or medical tool the method comprising the steps of positioning a pre-fluted blank 14 including a stem 24 and a shank 22 within a machine 30, using a probe to identify a position and/or an orientation of at least one flute 26 of the pre-fluted blank 14 and/or the position and/or orientation of an orientation indicator 28 of the pre-fluted blank 14, and using the machine 30 to form a cutting end region 36 at the end of the stem 24 of the pre-fluted blank 14 remote from the shank 22, the flute 26 extending into the cutting end region 36, the machine 30 being controlled to ensure that the cutting end region 36 is correctly orientated relative to the flutes 26 of the pre-fluted blank 14.

12 Claims, 3 Drawing Sheets

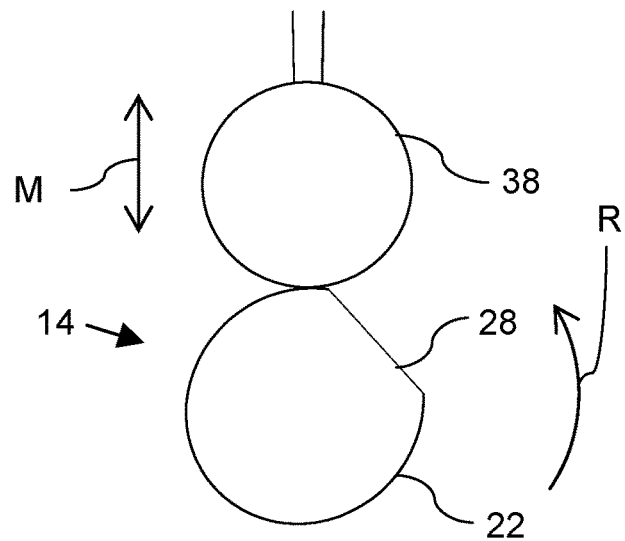
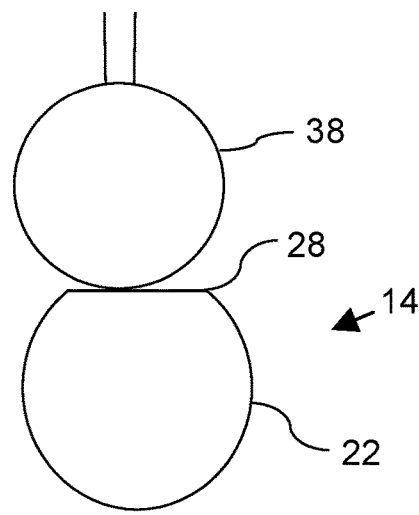
Figure 4A
Figure 4B
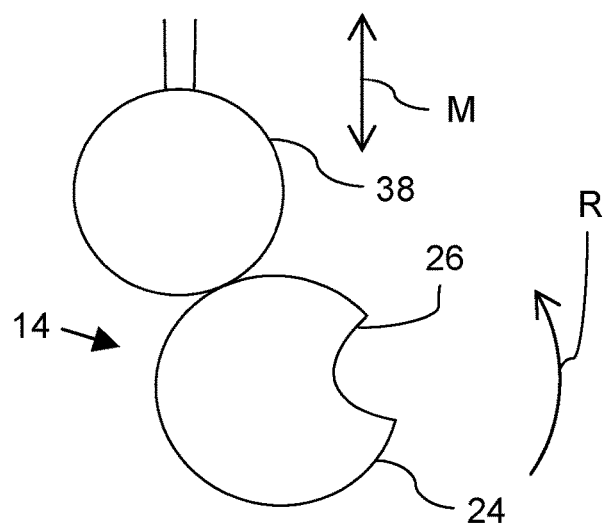
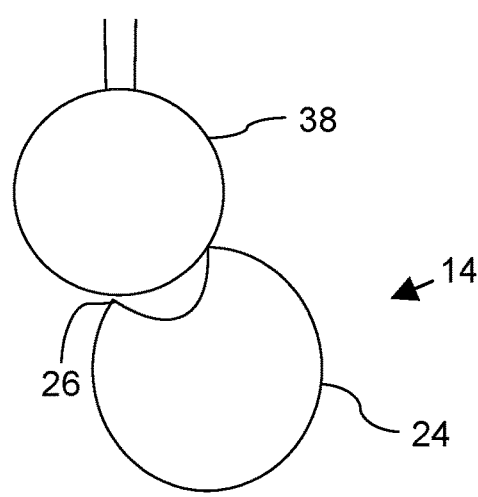
Figure 5A
Figure 5B

MANUFACTURE OF A DENTAL TOOL

FIELD OF THE INVENTION

This invention relates to a method for use in the manufacture of a tool such as a milling tool for use in dental applications, and in particular for use in the milling of materials during the manufacture of a dental prosthesis such as a crown, bridge or denture.

BACKGROUND

United Kingdom Patent publication GB2573524 describes a milling tool for use in dental applications, the milling tool comprising a shank for receipt by the chuck of a milling machine, a fluted stem projecting coaxially from the shank, and a ball-nosed end region into which the flutes of the fluted stem project and defining a cutting face or profile which, in use, engages a block of material to be milled using the tool to mill or to remove material from the block to form the block to a desired shape or profile.

The milling tool is typically manufactured by taking a blank of uniform diameter, for example of rod of tungsten carbide or another suitable material, and cutting it in such a manner as to result in the formation of a shank and a stem extending from the shank. Then, with such a shaped blank installed within a suitable grinding machine, material is removed from the blank, typically in several grinding operations in sequence, to form the blank to the shape outlined hereinbefore, forming the flutes upon the stem, and forming the ball-nosed end region. Typically, the shaping or forming of a blank to the required form is a time consuming, slow operation. Similar methods are used in the manufacture of tools with other end profiles such as bull-nosed tools.

International patent publication WO2019197931A1 describes a method of grinding a helical groove into a plain blank workpiece using a grinding wheel. WO2019197931A1 is concerned with the dimensions of the grinding wheel and position-dependent inaccuracies of the various components used in the method. The method comprises forming a calibration groove to identify the location of the helical groove. The helical groove is cut at the location of the calibration groove, and the calibration groove is no longer present after formation of the helical groove.

Japanese patent publication JPH03104549A discloses a process of making a notch on a plain blank in which the notch serves as an index for a grinding machine to grind helical flutes onto the plain blank.

Whilst such techniques result in the formation of a tool of a desired shape, it is thought that the manufacturing methods are inefficient. It is an object of the invention to provide a method for use in the manufacture of a tool in which at least some of the disadvantages associated with known manufacturing methods are overcome or are of reduced effect.

SUMMARY OF THE INVENTION

According to a first aspect of the invention there is provided a method for manufacturing a dental or medical tool, the method comprising the steps of positioning within a machine a pre-fluted blank comprising at least one flute, the blank including a stem and a shank, using a probe to identify an orientation and/or a position of the at least one flute of the pre-fluted blank, and using the machine to form a cutting end region at the end of the stem of the pre-fluted blank remote from the shank, the flute extending into the cutting end region, the machine being controlled to ensure that the cutting end region is correctly orientated relative to the flutes of the pre-fluted blank.

The probe may comprise a physical probe which contacts the pre-fluted blank, in use, to identify the orientation thereof. Alternatively, it may comprise, for example, an optical probe which does not contact the pre-fluted blank. The probe may identify the position and/or orientation of a flute of the pre-fluted blank directly, or alternatively may be operable to detect the position and/or the orientation of an orientation indicator provided on the pre-fluted blank.

The machine may be used to form other features on the pre-fluted blank. By way of example, it may involve cutting or shaping a land and/or relief at a location along the flute.

It will be appreciated that by using the method of the invention, the pre-fluted blank is formed as a separate operation to the formation of the cutting end region. If desired, it may be undertaken using a different machine to that used to form the cutting end region, although the same machine (or same type of machine) could be used to undertake both of these operations, and it could be undertaken at a different location, if desired. By way of example, a manufacturer specialising in the formation of cutting end regions and finishing of the tools may buy in pre-fluted blanks from another supplier, potentially leading to significant manufacturing efficiencies for the manufacturer.

According to a second aspect of the invention, there is provided a method for manufacturing a tool the method comprising the steps of, in a first machine, forming a rod of material to a shape including a shank and a stem extending coaxially from the shank, the stem including, upon its outer surface, at least one generally helical flute, and thus forming a pre-fluted blank, and forming an orientation indicator upon the pre-fluted blank indicative of the orientation of the flutes thereon.

A rod of material may be understood in the art as a 'blank', or dental blank, and may be a rod of specific length, for instance 33 mm, and a specific diameter, typically in the region of 2 mm to 6 mm. Where an orientation indicator is provided on the pre-fluted blank, by using the machine used to form the pre-fluted blank to also apply the orientation indicator to the pre-fluted blank, and subsequently using the orientation indicator when forming the cutting end region, it will be appreciated that it can be ensured that the machining of the cutting end region, and other features formed on the tool, is properly aligned with the flute or flutes formed on the pre-fluted blank.

The orientation indicator may comprise, for example, a flat, groove, recess or upstand provided on the pre-fluted blank. By way of example, it may be provided upon the shank, conveniently adjacent the stem. However, the invention is not restricted in this regard, and the orientation indicator could be located elsewhere.

The tool may be of the form described and illustrated in GB2573524. However, it will be appreciated that the tool need not be of precisely this form and that variations or modifications may be made thereto without departing from the scope of the invention as defined by the appended claims. Thus, the invention may be employed in the manufacture of, for example ball-nosed, bull-nosed or flat ended milling tools, drilling tools and the like, and may be employed in the fabrication of tools with any number of flutes. The invention further relates to a pre-fluted blank comprising a shank and a stem extending coaxially from the shank, the stem including, upon its outer surface, at least one generally helical upstanding flute, and an orientation indicator formed on the shank or the stem. The invention further relates to a milling tool manufactured in accordance with the method set out hereinbefore.

The invention will further be described, by way of example, with reference to the accompanying drawings, in which:

DESCRIPTION OF THE FIGURES

FIGS. 4A and 4B are a schematic illustration of an exemplary probing procedure;

FIGS. 5A and 5B are a schematic illustration of another exemplary probing procedure.

DESCRIPTION

Figure 6:
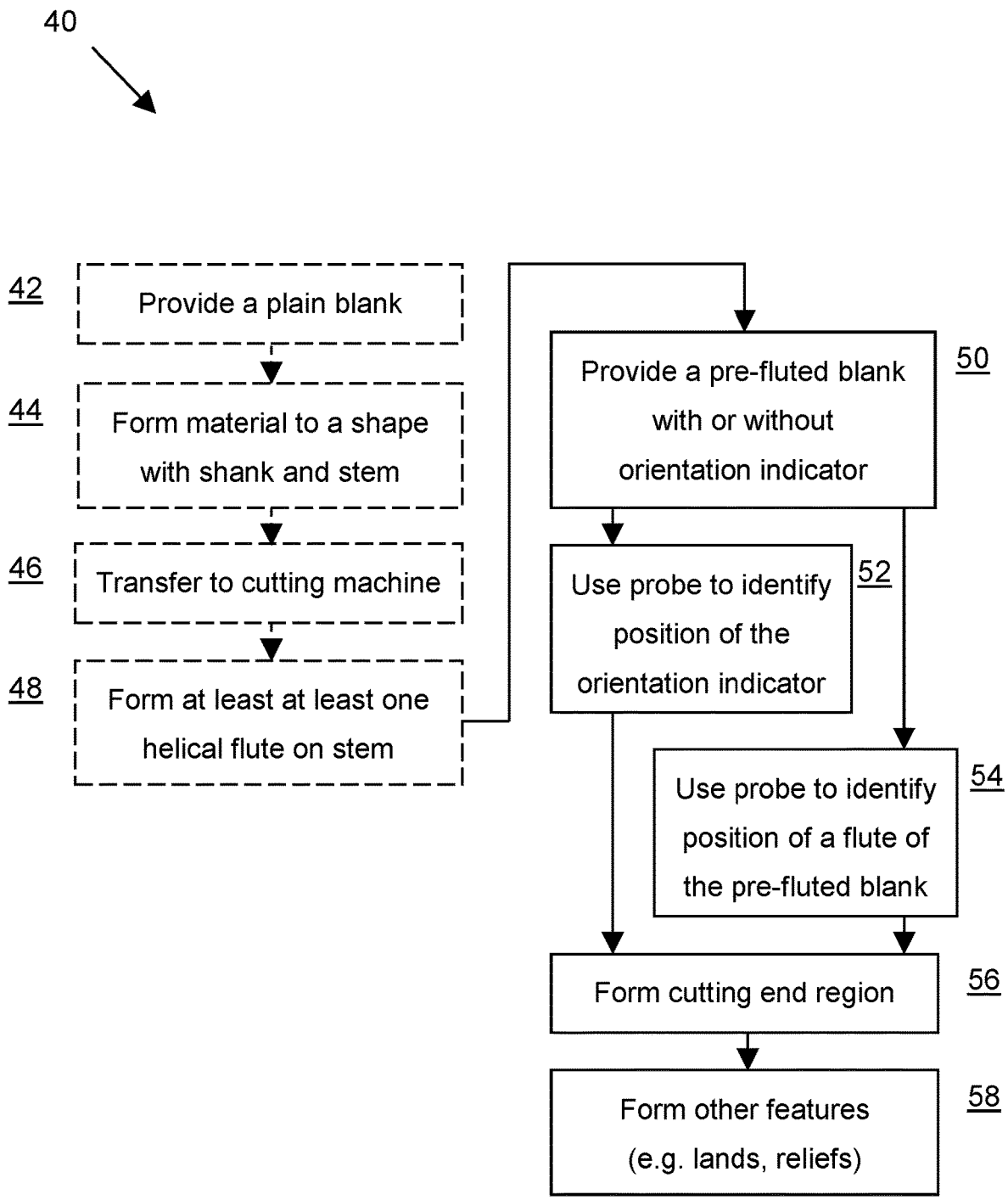
FIG. 6 is a schematic flow diagram illustrating exemplary steps of a method used in aspects of the invention.

Referring to the accompanying drawings, a method 40 for use in the manufacture of a milling tool 10 is illustrated. The method 40 is undertaken in two main stages. In a first stage or operation, a rod 12 is provided that constitutes a plain blank, the rod 12 being of a suitable material, for example tungsten carbide or another suitable hard, wear resistant material. The rod 12 is machined to form it into a pre-fluted blank 14. In the second stage or operation, the pre-fluted blank 14 is machined to form it into the shape of the final milling tool 10. Referring to FIG. 6, the first stage may comprise steps 42 to 48 that will be described below. The second stage may comprise steps 50 to 58 described below. The present invention relates primarily to the second of these stages or operations, as illustrated by the right hand part of FIG. 1 and by steps 50 to 58 of FIG. 6, making use of a pre-fluted blank 14 manufactured in the first stage as illustrated by the left hand side of FIG. 1 and by steps 42 to 48 of FIG. 6.

Figure 1:
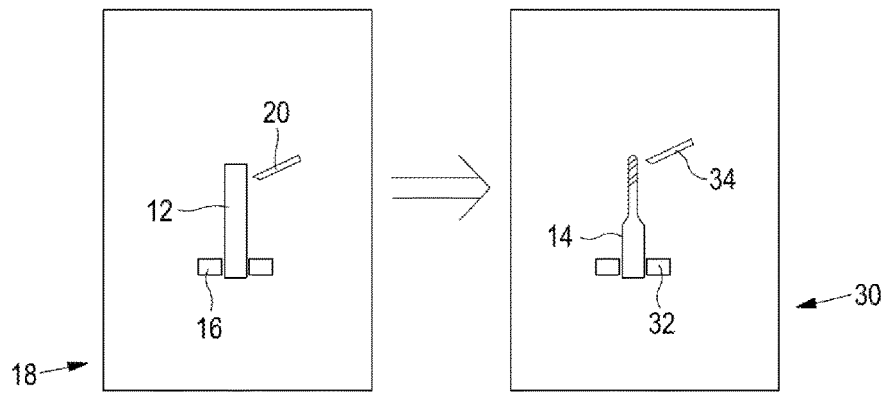
FIG. 1 is a diagrammatic view illustrating steps in a method of manufacture of a dental tool, part of which constitutes an embodiment of the invention.

As shown in FIG. 1, in the first stage, the rod 12 is placed into a support 16 forming part of a first machine 18. A cutter in the form of a grinding wheel 20 or the like of the first machine 18 is then moved to a position in which it is able to bear against the surface of the rod 12, cutting or grinding material therefrom to form the rod 12 into the shape of the pre-fluted blank 14. Specifically, the cutter 20 forms the rod 12 to a shape including a relatively large diameter shank 22, and a smaller diameter stem 24 projecting co-axially from the shank 22, the manner in which the stem 24 is formed also resulting in the formation of at least one generally helical groove or flute 26 formed integrally with the stem 24, the flute 26 extending along a significant part of the length of the stem 24. The flute 26 may be formed, if desired, using a suitable cutting or grinding procedure, and the formation of the flute 26 results in the stem 24 being shaped to include one or more integral upstands or ribs 26a, formed integrally with the stem 24. In the arrangement illustrated, three flutes 26, and three upstands or ribs 26a, are provided. However, it will be appreciated that the invention is not restricted in this regard, and arrangements including fewer flutes, for example one or two flutes, or a greater number of flutes such a four or more flutes, are also possible without departing from the scope of the invention. While the flutes 26 extend to an end 24a of the stem 24, the end 24a is otherwise left untreated. As such, the end 24a of the stem 24 is not shaped to a particular cutting shape, and therefore is characterised by the absence of a cutting end such as a ball-nosed end, flat ended, bull-nosed end, or otherwise. The end 24a is not provided with a surface finish and can be considered unfinished. A pre-fluted blank 14 may be characterised by the presence of an unfinished end 24a.

In addition, whilst the rod 12 is fitted to the support 16, the first machine 18 is preferably operable to form an orientation indicator 28 onto the shank 22 (although in some arrangements, the formation of such an orientation indicator 28 may be omitted). The orientation indicator 28 conveniently takes the form of a flat or a groove or recess cut into the shank 22, for example on a part thereof spaced significantly from the stem 24. However, the axial position of the orientation indicator 28 is not of importance to the invention and it may be located elsewhere, for example on a part of the shank 22 adjacent the stem 24 (as illustrated), or on the stem 24 itself. Furthermore, rather than take the form of a flat, groove, or recess, the orientation indicator 28 could take the form of a projection upstanding from the surface of the stem 24 or shank 22. Likewise, the orientation indicator 28 may be provided in the form of a surface marking such as a dye or etching such as a laser-etching. The purpose of the orientation indicator 28 is to provide a datum indicative of the angular orientation and/or position of the flute or flutes 26 for use during subsequent stages in the manufacturing process. It will be appreciated that the orientation indicator 28, having been created after formation of the flutes 26, is detectable by an orientation probe.

Whilst the description hereinbefore is of an arrangement in which the first operation is undertaken using a single first machine, as described hereinbefore it may be undertaken using several machines in sequence. For example, one machine may be used to form the stem, and another may be used to form the flute upon the stem. The term "first machine" as used herein is intended to cover both situations, and so may refer to more than one machine where the first operation is undertaken using a plurality of machines. Where two or more machines are used in performing the first operation, the orientation indicator (see below) is preferably formed using the same machine as that used to form the flute, so as to ensure that the orientation indicator is properly aligned or orientated relative to the flute.

After manufacture of the pre-fluted blank 14, the blank 14 is removed from the first machine 18 and positioned within a second machine 30, supported by a support 32 thereof.

In accordance with the invention, the second machine includes a sensor or probe that is operable to detect the orientation of the pre-fluted blank 14, and hence the positions of the flutes thereof. This may be achieved by identifying, using the probe, the orientation and/or location of the orientation indicator 28, where provided, or may be achieved by directly sensing the position and/or orientation of at least one of the flutes of the pre-fluted blank 14.

The method may include detecting the location of an end, such as the shank end or the stem end 24a, of the pre-fluted blank 14 to derive therefrom the orientation and/or position of the flute relative to the end of the blank. The probe conveniently comprises a physical probe that contacts the pre-fluted blank 14 and outputs information that can be used to identify the orientation of the pre-fluted blank. Alternatively, it could comprise an optical probe, for example, that does not physically contact the pre-fluted blank 14. The position or orientation information derived through the use of the probe is supplied to control unit of the second machine 30 for use in controlling the operation thereof.

FIGS. 4A, 4B, 5A and 5B schematically illustrate one example of a probing method, using a mechanical probe tip 38 to detect the orientation of a pre-fluted blank 14. FIGS. 4A and 4B illustrate a section of the shank 22, taken perpendicularly to the shank axis, the shank 22 having been provided with an orientation indicator 28 in the form of a flat portion cut into the shank 22. The probe tip 38 is brought into sensing range with the pre-fluted blank 14, for instance into physical contact, by moving it along a movement axis M (e.g., towards and away from the pre-fluted blank). As the pre-fluted blank 14 is axially rotated, for instance in the direction of the arrow R, the probe tip 38 follows the circumferential contour of the shank 22, and therefore the contour of the pre-fluted blank 14. It will be understood that the probe tip 38 may be moveable, or may be held in a fixed position allowing it to deflect when encountering a structure and/or to relax into a rest position in the absence of a structure, to thereby detect a change of a degree of deflection of it. Other probing principles may be used.

As illustrated in FIG. 4A, while the probe tip 38 follows a circular contour, no movement is expected of the probe tip 38 neither towards nor away from the pre-fluted blank 14. Turning to FIG. 4B, as the probe tip 38 engages the flat portion of the orientation indicator 28, it is able to move further towards the axis of the shank 22. Thereby the orientation of the pre-fluted blank 14 can be identified by way of a different (i.e., more or less) displacement, relative to a reference position, of the probe tip 38. As will be appreciated, other orientation indicator geometries may be used to result in correspondingly different probe behaviour to be observed. The size and form of the orientation indicator may depend on the probe design. Some high precision/high accuracy probes may have a tip diameter in the region of a few millimetres, in a similar region or even larger than the shank diameter or the size of the orientation indicator.

FIGS. 5A and 5B illustrate another example of a probing method, and show a section of a stem 14, the section taken perpendicularly to the stem axis, the stem 14 being provided with a flute 26. Only one flute 26 is illustrated in FIGS. 5A and 5B, although the stem 14 may have been provided with two, three, or more flutes. Similarly to the sequence of FIGS. 4A and 4B, in FIG. 5A the pre-fluted blank is rotated while the probe tip 38A is brought into sensing range, e.g. into contact, with the surface of the stem 24. Axial rotation of the pre-fluted blank 14 allows the probe tip 38 to follow the circumferential contour of the pre-fluted blank 14, in this instance the contour of the stem 24. As shown in FIG. 5B, at a location of a flute 26 the probe tip 38 may experience a displacement towards the stem axis. The probing principle may be similar or identical to that described in relation to FIGS. 4A and 4B. A displacement of the probe tip 38 can then be correlated with the orientation of the flute 26.

While the examples of FIGS. 4A, 4B, 5A and 5B show a mechanical probe tip 38, other probe systems may be used, such as other mechanical probing principles or optical systems such as laser-based distance measurements may be used instead or in addition.

The second machine 30 includes a cutter in the form of a grinding wheel 34 operable to cut or grind the end part of the stem 24 remote from the shank 22 to form a cutting end region 36 thereon, for example of ball-nosed, bull-nosed or flat ended form. The operation of the grinding wheel 34 involves removing parts of the ends of the upstands or ribs 26a to form the cutting end region 36. As a result of the formation of the cutting end region 36, the unfinished end 24a may be shaped or removed. It will be appreciated that, as shown, the flutes 26 extend into the cutting end region 36.

The grinding wheel 34 is further used to generate a required land width and relief along the upstands or ribs 26a. In order to achieve all of this, it is important for the control unit of the second machine to have knowledge of the position and/or the orientation of at least one flute 26, hence the need use a sensor or probe to detect the position of the orientation indicator 28 as described hereinbefore, or to directly identify the orientation of the at least one flute 26, and control the operation of the machine 30 accordingly. The position of the flute 26 may be determined by detecting the end location of the pre-fluted blank 14, and determining the position of the flute 14 with reference to the end location.

Figure 3:
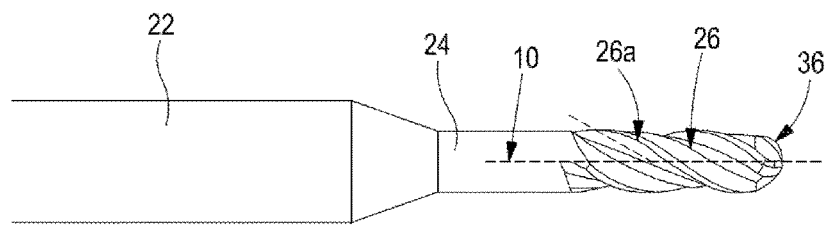
FIG. 3 is a view illustrating a finished milling tool.

The method may include a peeling step in which a peeling region of the shank 22, constituted by a region of the shank 22 adjacent the stem 24, is machined to remove portions thereof, to reduce the diameter of the peeling region to the diameter of the stem 24. The peeling step provides, effectively, a longer stem. The peeling step may result in a removal of an orientation indicator 28 located in the peeling region, as illustrated in FIG. 3 by the absence of an orientation indicator 28. In embodiments of the invention, the method may comprise providing the orientation indicator 28 in a peeling region of the pre-fluted blank 14. In that manner, the tool 10 in its final form has no orientation indicator.

After machining of the tool 10 using the second machine 30, the tool 10 is removed from the second machine 30, and a hard material coating or the like may be applied thereto to enhance the wear resistance and extend the useful working life of the tool 10.

Figure 2:
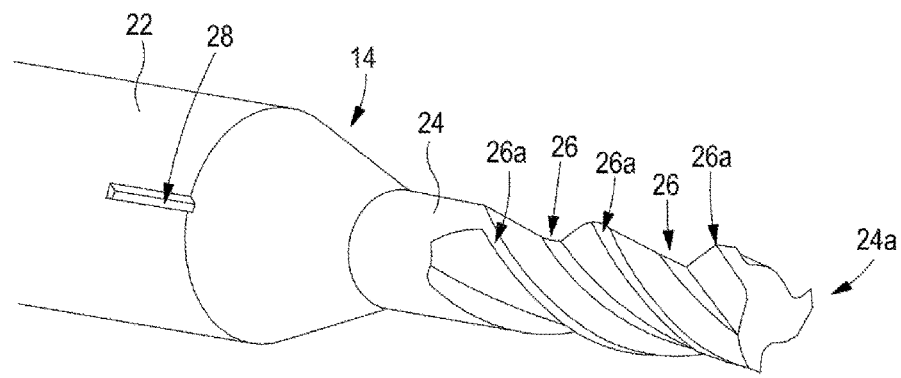
FIG. 2 is a diagrammatic view illustrating part of a pre-fluted blank.

Accordingly, the method 40 comprises a step 50 of providing a pre-fluted blank. The pre-fluted blank may be provided, for instance, by sourcing it from a supplier. The pre-fluted blank may be manufactured from a plain blank. To this end, in a variation of the method 40, an optional step 42 comprises providing a plain blank. In an optional step 44, a shank and coaxial stem may be formed in the plain blank. Step 44 may be omitted in embodiments using a blank with uniform diameter having a shank region and a stem region. In a step 46, at least one helical flute is formed on the stem, or in the stem region, to thereby form the pre-fluted blank. Steps 44 and 46 may be carried out contemporaneously or as different forming operations, but this is not necessarily the case in all embodiments. In accordance with the invention, as part of step 48 or of step 50, an orientation indicator may be formed on the pre-fluted blank. A pre-fluted blank may be recognised by its unfinished end, or tip, to (such as the end 24a in FIG. 2) and one or more flutes 26 extending to the unfinished end. Once transferred and located in a cutting machine for end cutting, a probe is used to identify the position and/or the orientation of a reference point of the pre-fluted blank. In step 52, the position and/or the orientation of an orientation indicator 28 is determined using a probe. As an alternative or concurrently to step 52, step 54 may be carried out in which the position and/or orientation of at least one flute of the pre-fluted blank is determined using a probe. It will be appreciated that the method 40 may, in one variant, start with step 50 in which a pre-fluted blank is provided and positioned in a forming machine, followed by step 54, for instance if the pre-fluted blank is not provided with an additional orientation indicator 28. In a step 56, the cutting end region of the pre-fluted blank is formed. In step 56, the unfinished region of the end 24a is formed into a cutting end such as a ball-nosed, flat ended, or bull-nosed end. In a step 58, other features such as lands and reliefs are formed at locations along the flutes 26 on the pre-fluted blank. Steps 56 and 58 are conveniently carried out in the same machine, although the invention is not necessarily so limited.

It will be appreciated that the sequence of steps is exemplary and some of the steps may be carried out in a different order and/or contemporaneously.

The use of the invention is advantageous in that manufacturing efficiencies may be made, using machines or equipment specifically adapted for use in the steps of the process. The stages of the manufacturing process need not be conducted in the same location as one another, for example the first machine may be located at a first site, from where the pre-fluted blanks 14 are dispatched to a second site at which the second machine 30 is located. A time consuming part of the manufacturing process is the completion of the first stage mentioned hereinbefore. It is envisaged that by having this stage completed elsewhere, a manufacturer specialising in the formation of the cutting end region and other finishing processes may make significant time savings and efficiency enhancements through using pre-fluted blanks, using the method of the invention to ensure that machining thereof is undertaken correctly. While it will be appreciated that the method requires additional time, compared to a conventional manufacturing methods, to position a pre-fluted blank in a machine and to identify the position and/or location of a flute or a separate orientation indicator, as applicable, the overall manufacturing time may be reduced. By way of example, time savings in the region of 20% or more may be made, thus the invention can lead to significant manufacturing efficiencies.

To illustrate the benefits of the invention with an illustrative example, the manufacture of a conventional tool requires a number of grinding operations to be carried out at the stem to create features such as flutes, lands, end formations such as a ball end, bull end, or flat end, etc., to turn the stem into a body of a milling tool. Of these grinding operations, the fluting operation is typically the most complex operation. The time required for forming flutes varies depending on tool head diameter, shank diameter, length of flute, etc. and may amount to 20% or more of the total manufacturing time excluding setup time for a tool. It will be understood that the time savings may depend on the size of the tool and, consequentially, the time required to position a pre-fluted blank, and to identify the position and/or orientation of the flutes on it.

The exemplary pre-fluted blank described herein comprises a shank with larger diameter than the stem, in which a shank region and a stem region can be visually distinguished. However, the invention is not so limited. Some blanks may comprise a stem and shank of the same diameter, the stem region of the pre-fluted blank being identifiable by the location and extension of the flutes.

Whilst a specific embodiment of the invention is described hereinbefore with reference to the accompanying drawings, it will be appreciated that a wide range of modifications and alterations may be made thereto without departing from the scope of the invention as defined by the appended claims.

The invention claimed is:

1. A method for manufacturing a dental or medical tool, the method comprising the steps of:
    positioning within a machine a pre-fluted blank, the pre-fluted blank being a blank comprising at least one flute, the blank including a stem and a shank;
    using a probe to identify an orientation and/or position of the at least one flute of the pre-fluted blank; and
    using the machine to form a cutting end region at the end of the stem of the pre-fluted blank remote from the shank, the flute extending into the cutting end region, the machine being controlled to ensure that the cutting end region is correctly orientated relative to the flutes of the pre-fluted blank,
    wherein the probe is a physical probe that contacts the pre-fluted blank.

2. The method according to claim 1, wherein the probe identifies the position or orientation of a flute of the pre-fluted blank directly.

3. The method according to claim 1, wherein the cutting end region is of ball-nosed, bull-nosed or flat ended form.

4. The method according to claim 1, wherein the machine is further used to form other features on or associated with the flute.

5. The method according to claim 4, wherein the other features comprise a land and/or a relief.

6. A milling tool manufactured in accordance with the method of claim 1.

7. The milling tool according to claim 6 and adapted for use in dental or medical applications.

8. A method for manufacturing a dental or medical tool, the method comprising the steps of:
    positioning within a machine a pre-fluted blank, the pre-fluted blank being a blank comprising at least one flute, the blank including a stem and a shank;
    using a probe to identify an orientation and/or position of the at least one flute of the pre-fluted blank; and
    using the machine to form a cutting end region at the end of the stem of the pre-fluted blank remote from the shank, the flute extending into the cutting end region, the machine being controlled to ensure that the cutting end region is correctly orientated relative to the at least one flute of the pre-fluted blank,
    where the probe identifies the position or orientation of an orientation indicator provided on the pre-fluted blank.

9. The method according to claim 8, wherein the orientation indicator comprises a flat, groove or recess formed in the shank and/or stem.

10. A method for manufacturing a dental or medical tool, the method comprising the steps of:
    positioning within a machine a pre-fluted blank, the pre-fluted blank being a blank comprising at least one flute, the blank including a stem and a shank;
    using a probe to identify an orientation and/or position of the at least one flute of the pre-fluted blank; and
    using the machine to form a cutting end region at the end of the stem of the pre-fluted blank remote from the shank, the flute extending into the cutting end region, the machine being controlled to ensure that the cutting end region is correctly orientated relative to the at least one flute of the pre-fluted blank,
    wherein the method further comprises, in a first operation, forming a rod of material to a shape including the shank and the stem extending coaxially from the shank, the stem including, upon its outer surface, at least one generally helical flute, and thus forming the pre-fluted blank, and
    wherein the first operation further comprises forming an orientation indicator upon the pre-fluted blank indicative of the orientation of the at least one flute thereon.

11. The method according to claim 10, wherein the machine used in the first operation and that used in the formation of the cutting end region are different machines.

12. The method according to claim 11, wherein the different machines are located remotely from one another.

* * * * *